(12) United States Patent  
Jeong

(10) Patent No.: US 9,221,128 B2  
(45) Date of Patent: Dec. 29, 2015

(54) METHOD OF INSPECTING A SOLDER JOINT

(71) Applicant: KOH YOUNG TECHNOLOGY INC., Seoul (KR)

(72) Inventor: Joong-Ki Jeong, Seoul (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 25 days.

(21) Appl. No.: 14/073,199

(22) Filed: Nov. 6, 2013

(65) Prior Publication Data

US 2014/0133738 A1 May 15, 2014

(30) Foreign Application Priority Data

Nov. 12, 2012 (KR) .................. 10-2012-0127238

(51) Int. Cl.  
*G06K 9/00* (2006.01)  
*B23K 31/12* (2006.01)  
*G06T 7/00* (2006.01)  
*G01N 21/956* (2006.01)

(52) U.S. Cl.  
CPC ........ *B23K 31/125* (2013.01); *G01N 21/95684* (2013.01); *G06T 7/0004* (2013.01); *G06T 2207/30141* (2013.01); *G06T 2207/30152* (2013.01)

(58) Field of Classification Search  
CPC . B23K 31/125; G01N 21/8806; G06T 7/0004  
USPC ........................ 382/150, 132; 365/625, 394  
See application file for complete search history.

(56) References Cited

U.S. PATENT DOCUMENTS 5,064,291 A * 11/1991 Reiser ........................ 356/625

FOREIGN PATENT DOCUMENTS

| JP | 02-091505 | 3/1990 |
| JP | 03-183906 | 8/1991 |
| JP | 09-089525 | 4/1997 |
| JP | 09-321500 | 12/1997 |
| JP | 10-141929 | 5/1998 |
| JP | 2002-022412 | 1/2002 |
| JP | 2002-107311 | 4/2002 |
| JP | 2009-300429 | 12/2009 |
| JP | 2010-091569 | 4/2010 |
| JP | 2011-013220 | 1/2011 |
| JP | 2011-220934 | 11/2011 |

* cited by examiner

*Primary Examiner* — Ruiping Li  
(74) *Attorney, Agent, or Firm* — Kile Park Reed & Houtteman PLLC

(57) ABSTRACT

A method of inspecting a solder joint through which a lead of a semiconductor device is mounted on a printed circuit board is disclosed. The method includes setting an estimated solder joint region at an outside of an end of the lead of the semiconductor device, capturing an image of the estimated solder joint region, calculating a height of solder joint in the estimated solder joint region by using the captured image of the estimated solder joint region, and determining whether the solder joint is defective by comparing the height of the solder joint in the estimated solder joint region with a reference height of a solder joint, which is previously set. According to the method, reliability of inspection is enhanced regardless of environmental noises.

6 Claims, 6 Drawing Sheets

METHOD OF INSPECTING A SOLDER JOINT

CROSS REFERENCE TO RELATED APPLICATION

This application claims priority from and the benefit of Korean Patent Applications No. 10-2012-0127238 filed on Nov. 12, 2012, which is hereby incorporated by reference for all purposes as if fully set forth herein.

BACKGROUND OF THE INVENTION

1. Field of the Invention

Exemplary embodiments of the present invention relate to a method of inspecting a solder joint. More particularly, exemplary embodiments of the present invention relate to a method of inspecting a solder joint through which a lead of a semiconductor device is mounted on a printed circuit board (PCB).

2. Discussion of the Background

Generally, the solder joint, through which a lead of a semiconductor device is mounted on a printed circuit board, is inspected through the color of light captured by a camera, while irradiating RGB (red, green and blue) lights by RGB illuminators with different angles, respectively onto the solder joint.

FIGS. 1A and 1B are a cross-sectional view for explaining a conventional method of inspecting a solder joint.

Referring to FIGS. 1A and 1B, the RGB illuminators 210, 220 and 230 are arranged in clockwise direction over a solder joint 240 to irradiate RGB lights onto the solder joint 240 through the RGB illuminators 210, 220 and 230, respectively. Then, the solder joint 240 is inspected by determining color of light captured by a camera 250 disposed over the solder joint 240.

In detail, when the solder joint 240 is good as shown in FIG. 1A, the solder joint 240 is formed to have slant surface decreasing height from the end portion of the lead 260. Therefore, the blue light illuminated by the B illuminator 230 is captured by the camera 250.

On the other hand, when the solder joint 240 is defective such as no solder or cold solder as shown in FIG. 1B, the solder joint is not formed at the end portion of the lead 260 and the solder has relatively flat surface. Therefore, the red light illuminated by the R illuminator 210 is captured by the camera 250.

However, according to the conventional method of inspecting solder joint, using the RGB illuminators 210, 220 and 230, reliability of inspection may be lowered due to the interference of environmental light and the interference of adjacent elements.

SUMMARY OF THE INVENTION

Exemplary embodiments of the present invention provide a method of inspecting a solder joint through which a lead of a semiconductor device is mounted on a printed circuit board. The method includes setting an estimated solder joint region at an outside of an end of the lead of the semiconductor device, capturing an image of the estimated solder joint region, calculating a height of solder joint in the estimated solder joint region by using the captured image of the estimated solder joint region, and determining whether the solder joint is defective by comparing the height of the solder joint in the estimated solder joint region with a reference height of a solder joint, which is previously set.

In this case, the estimated solder joint region may be set within a thickness region in a cad data of the lead.

For example, determining whether the solder joint is defective includes calculating a ratio of the height of the solder joint in the estimated solder joint region to the reference height of a solder joint, which is previously set, and determining whether the ratio of the solder joint is equal to or higher than a previously set ratio.

For example, the height of the solder joint in the estimated solder joint region may be an average height of the solder joint in the estimated solder joint region.

For example, the reference height of the solder joint may be a height of the estimated solder joint region.

According to the method of inspecting a solder joint, it is determined whether the solder joint is defective by comparing the height of the solder joint in the estimated solder joint region with a reference height of a solder joint, which is previously set, so that it is not affected by image noises induced by environment to improve reliability of inspection.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1A:
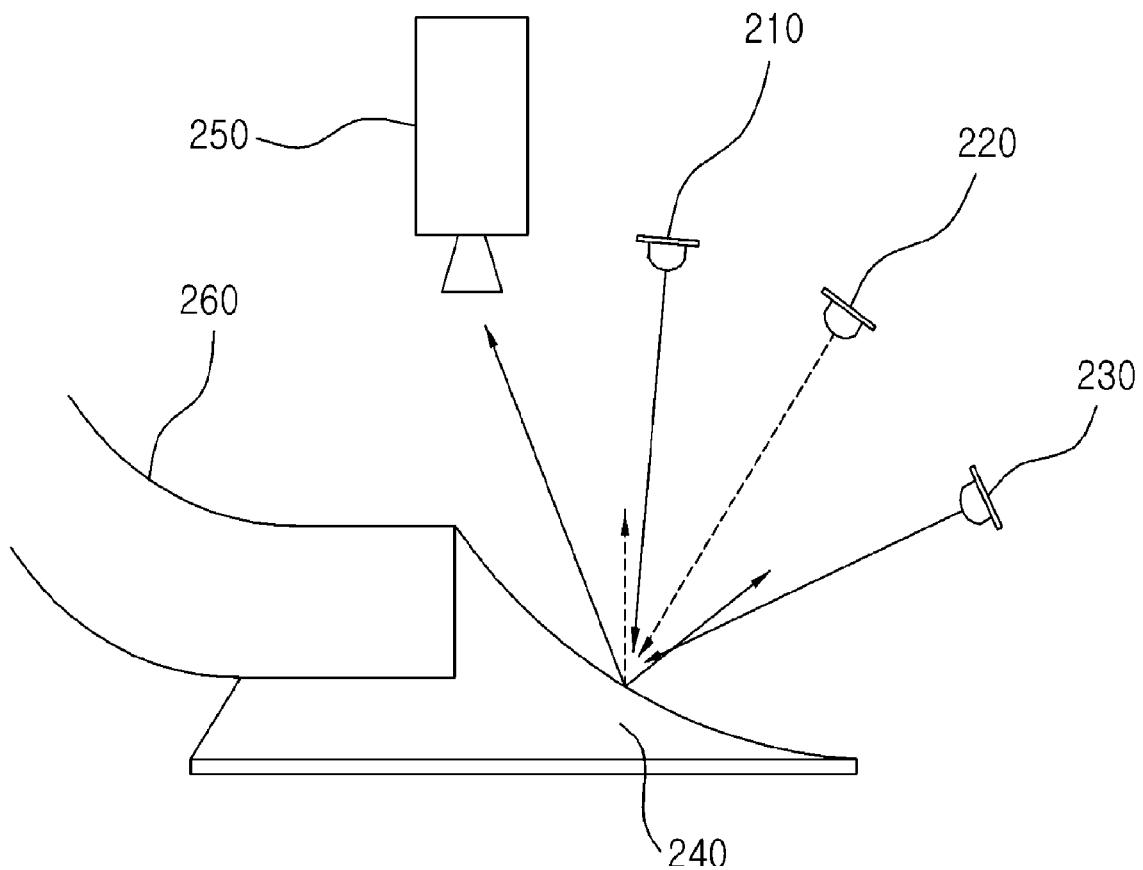
FIGS. 1A and 1B are a cross-sectional view for explaining a conventional method of inspecting a solder joint.
Figure 1B:
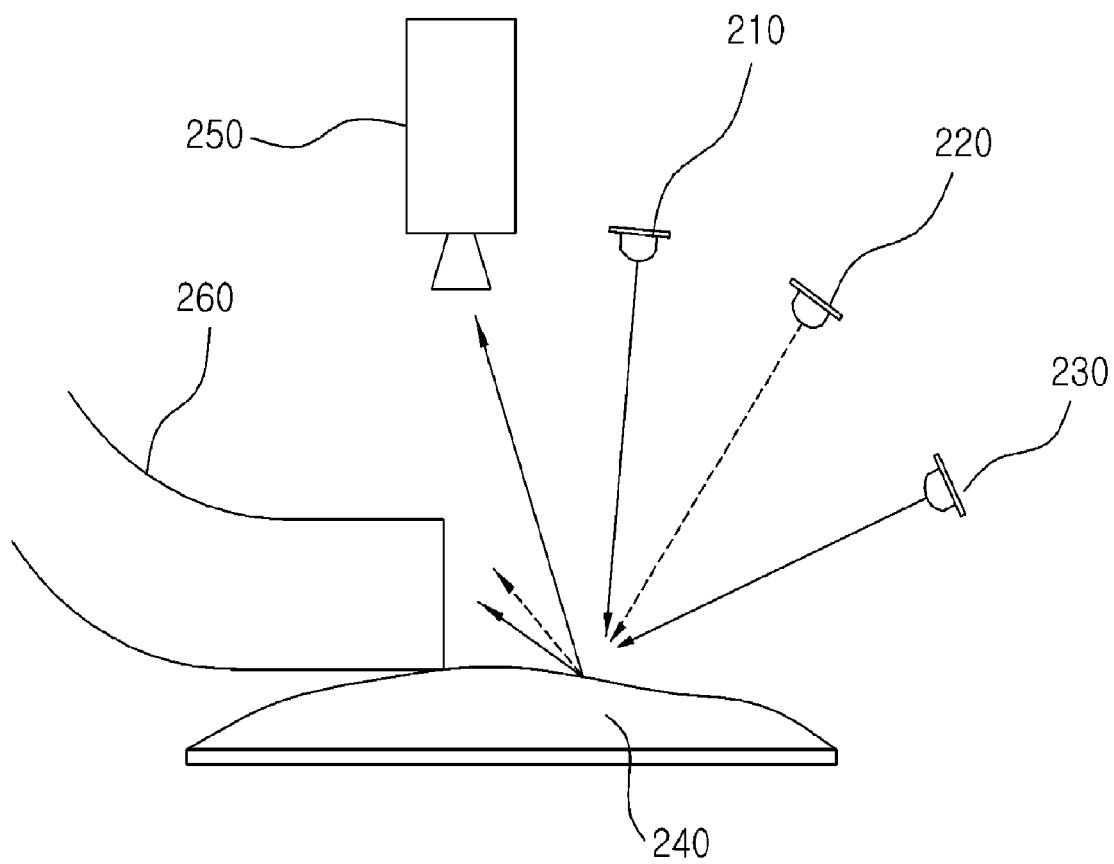

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings.

Figure 2:
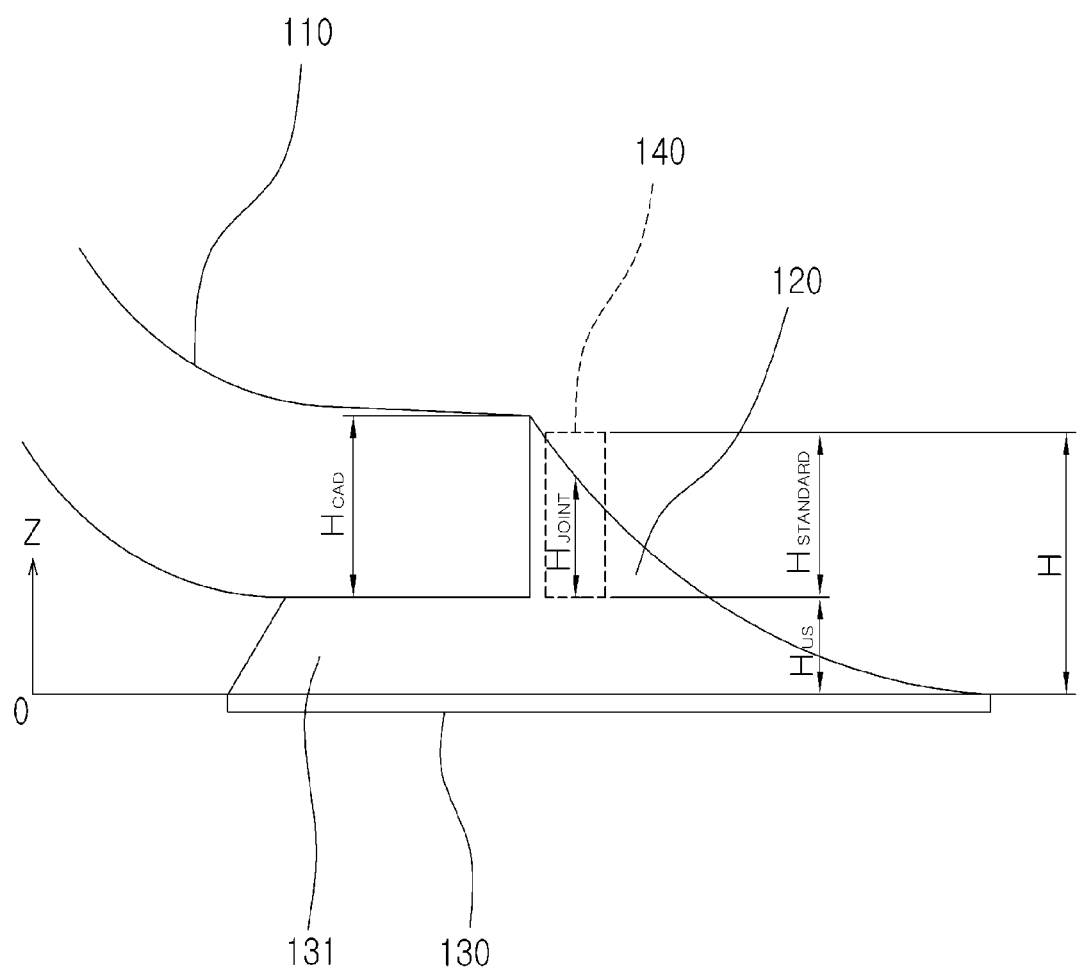
FIG. 2 is a cross-sectional view for explaining a method of inspecting a solder joint according to an exemplary embodiment of the present invention.
Figure 3:
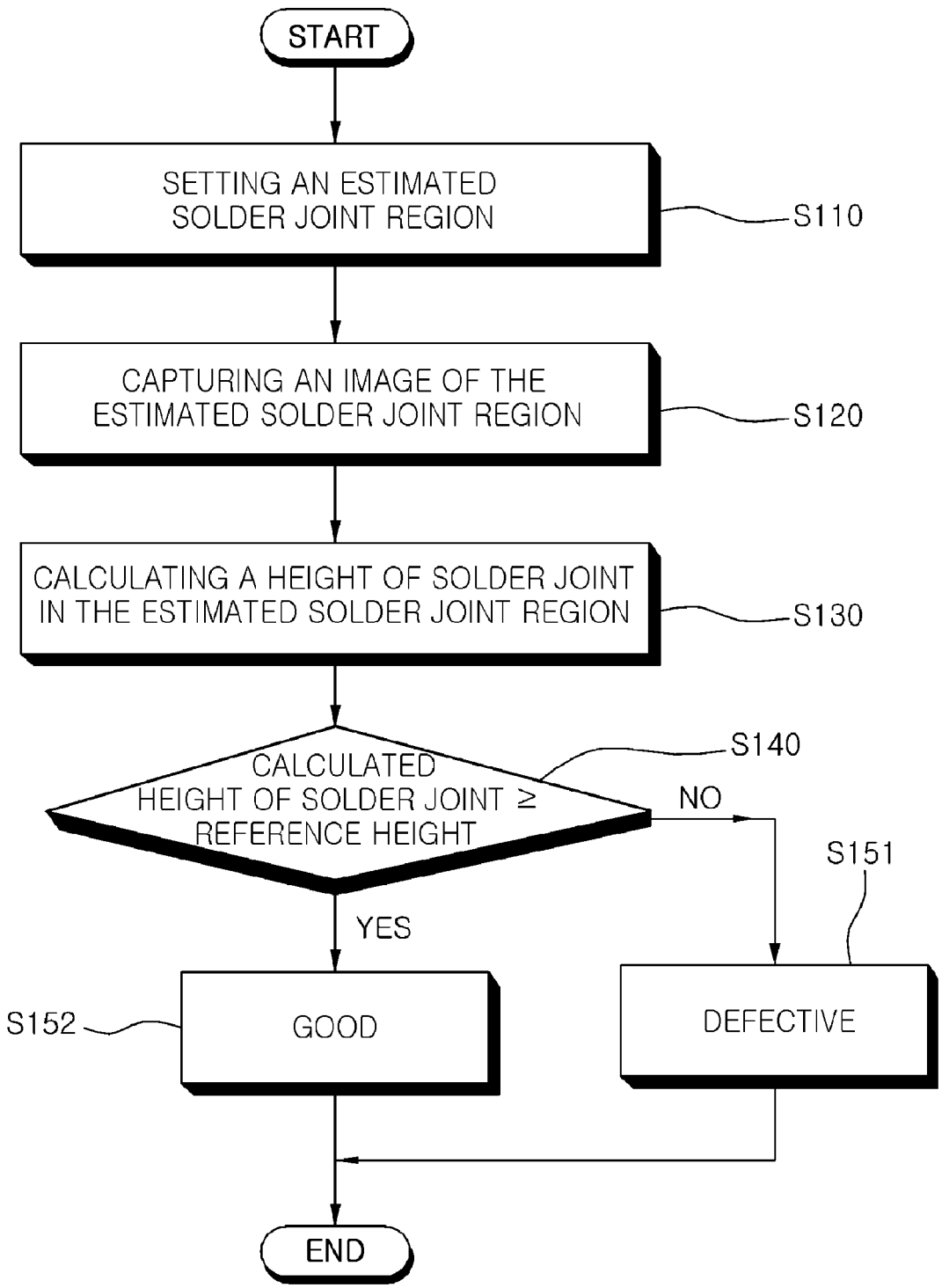
FIG. 3 is a block diagram for explaining a method of inspecting a solder joint according to an exemplary embodiment of the present invention.
Figure 4:
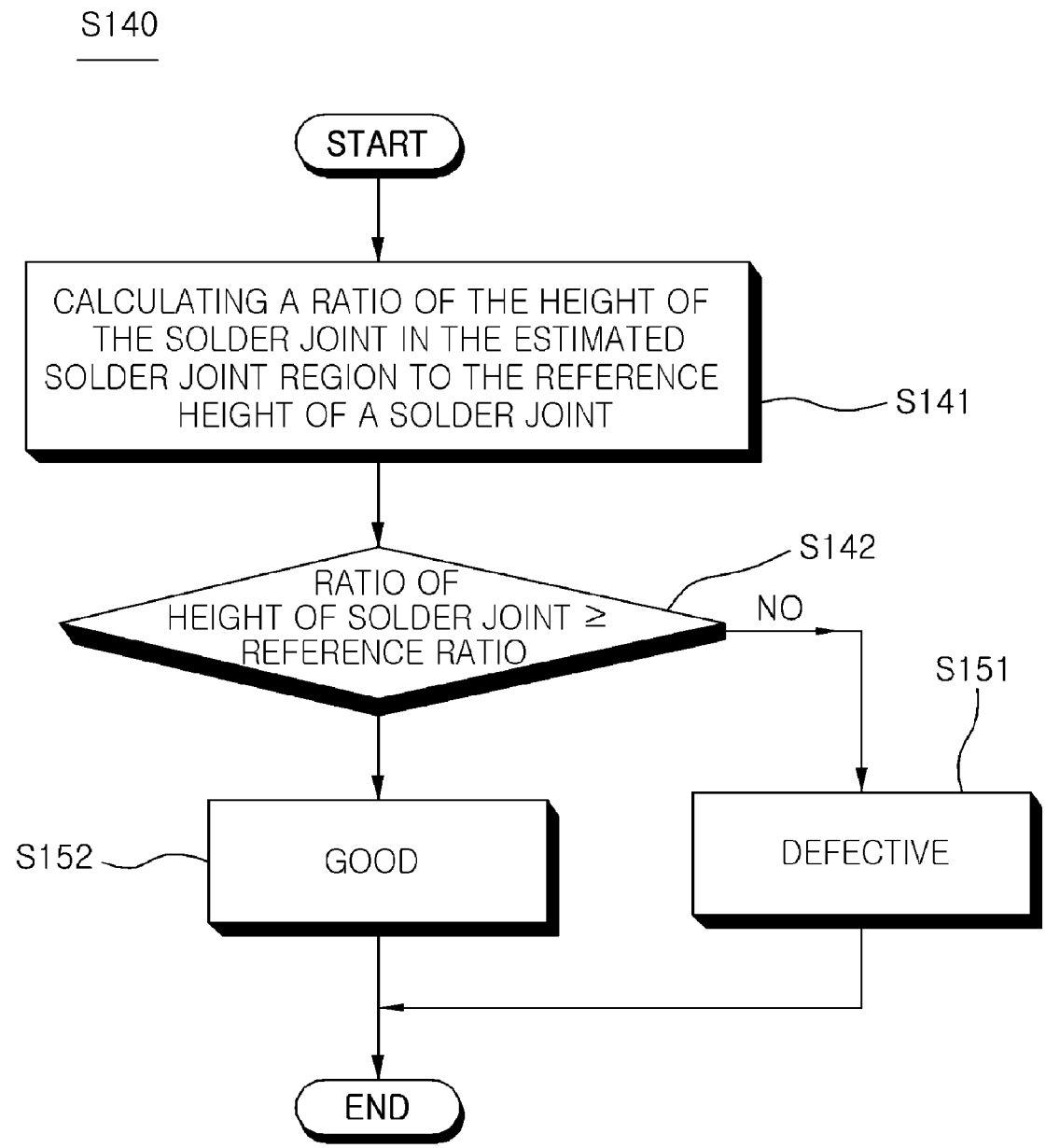
FIG. 4 is a block diagram for explain a step of determining whether the solder joint is defective.
Figure 5:
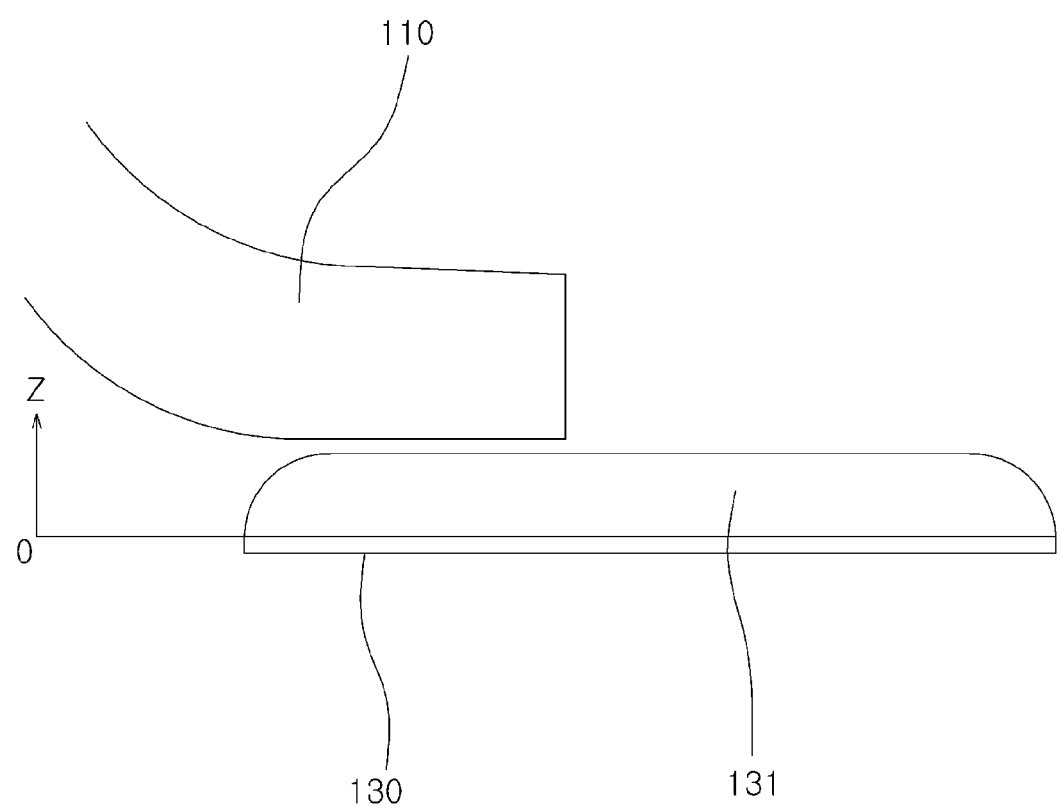
FIG. 5 is a cross-sectional view for explaining a reason why the estimated solder joint region is set within a thickness region in a cad data of a lead.

FIG. 2 is a cross-sectional view for explaining a method of inspecting a solder joint according to an exemplary embodiment of the present invention, FIG. 3 is a block diagram for explaining a method of inspecting a solder joint according to an exemplary embodiment of the present invention, FIG. 4 is a block diagram for explain a step of determining whether the solder joint is defective, and FIG. 5 is a cross-sectional view for explaining a reason why the estimated solder joint region is set within a thickness region in a cad data of a lead.

Referring to FIG. 2 through FIG. 5, according to a method of inspecting a solder joint of an exemplary embodiment of the present invention, an average height $H_{JOINT}$ of the solder joint 120 of end portion of a lead 110 is measured, and the average height $H_{JOINT}$ of the solder joint 120 is compared with a reference height $H_{STANDARD}$ of the solder joint 120, which is previously set, so that the solder joint 120 may be determined whether the solder joint 120 is defective regardless of the interference of environmental light and the interference of adjacent elements.

In detail, in order to inspect whether the solder joint 120, through which a lead of a semiconductor device is mounted on a printed circuit board 130, is defective according to an exemplary embodiment of the present invention, an estimated solder joint region 140 is set in a control section (not shown) (step S110).

Additionally, the reference height $H_{STANDARD}$ of the solder joint 120 at the estimated solder joint region 140 is also set in the control section. The reference height $H_{STANDARD}$ of the solder joint 120 may be changed in accordance with a size of the estimated solder joint region 140. For example, the reference height $H_{STANDARD}$ of the solder joint 120 is preferably set to be same height of the estimated solder joint region 140.

Further, it is preferable that the estimated solder joint region 140 is set within the thickness region in a cad data H.sub.CAD of the lead 110. In a cold solder case as shown in FIG. 5, the lead 110 of a semiconductor device may be separated from a pad 131 of a printed circuit board 130. Therefore, in order to inspect whether the solder joint 120 is defective more precisely, it is preferable that the estimated solder joint region 140 is set in the thickness region in a cad data H.sub.CAD not including a height H.sub.US of the pad 131. For example, it is preferable that the estimated solder joint region 140 is set to have a rectangular shape, when viewed along a widthwise direction of the lead 110 as shown in FIG. 2.

When the estimated solder joint region 140 is set, an image of end portions of the lead 110 of the semiconductor device, which includes an image of the estimated solder joint region 140, is captured through a camera (not shown) (step S120).

In this case, the height of the solder joint 120 in the estimated solder joint region 140 may be a height of one of some points of the solder joint 120 in the estimated solder joint region 140. However, according to the present embodiment, an average height $H_{JOINT}$ of the solder joint 120 is calculated to be the height of the solder joint 120 for precise inspection.

As shown in FIG. 2, when the height from the printed circuit board 130 to the end of the estimated solder joint region 140 is referred to as H, and the height of the pad 131 of the printed circuit board 130 is referred to as $H_{US}$, the average height $H_{JOINT}$ of the solder joint 120 in the estimated solder joint region 140 may be calculated by using the following Expression 1.

$$H_{JOINT} = \frac{\sum_{x,y \in ROI}(H(x, y) - H_{US}(x, y))}{\text{Total Pixels of } ROI} \qquad \text{Expression 1}$$

In this case, 'ROI' (region of interest) means the estimated solder joint region 140 in the image captured by the camera.

That is, the height H(x,y), which means the height of the end point of the solder joint with reference to the printed circuit board 130, is subtracted by the height $H_{US}(x,y)$ which means the height of pad 131 with reference to the printed circuit board 130 to get a real height of the solder joint at a position (x,y), and the real heights of the solder joint at a plurality of positions (x,y) in the ROI are summed to get summed real height. Then, the summed real height is divided by the number of positions (x,y) to get the average height $H_{JOINT}$ of the solder joint. Here, the number of positions (x,y) corresponds to the number of pixels in the ROI.

When the average height $H_{JOINT}$ of the solder joint is calculated, the control section compares the average height $H_{JOINT}$ of the solder joint with a reference height $H_{STANDARD}$ of the solder joint 120, which is previously set (step S140).

After comparing the average height $H_{JOINT}$ of the solder joint with a reference height $H_{STANDARD}$ of the solder joint 120, which is previously set, when the average height $H_{JOINT}$ of the solder joint is lower than the reference height $H_{STANDARD}$ of the solder joint 120, the control section determines that the solder joint is defective (step S151). When the average height $H_{JOINT}$ of the solder joint is equal to or higher than the reference height $H_{STANDARD}$ of the solder joint 120, the control section determines that the solder joint is good (step S152)

Referring to FIG. 4, determining whether the solder joint is defective will be explained in detail.

In order to determine whether the solder joint is defective, a ratio of the average height $H_{JOINT}$ of the solder joint 120 in the estimated solder joint region 140 to the reference height $H_{STANDARD}$ of a solder joint 120, which is previously set, is calculated by the control section (not shown) (step S141).

When the reference height of the solder joint 120, which is previously set, is referred to as $H_{STANDARD}$, the score that is the ratio of the average height $H_{JOINT}$ of the solder joint 120 in the estimated solder joint region 140 to the reference height $H_{STANDARD}$ of a solder joint 120, which is previously set, is express as the following Expression 2.

$$\text{Score} = \frac{H_{JOINT}}{H_{STANDARD}} \times 100 \ (\%) \qquad \text{Expression 2}$$

When the ratio (Score) of the average height $H_{JOINT}$ of the solder joint 120 in the estimated solder joint region 140 to the reference height $H_{STANDARD}$ of a solder joint 120 is calculated, the control section compares the ratio of the average height $H_{JOINT}$ of the solder joint 120 in the estimated solder joint region 140 to the reference height $H_{STANDARD}$ of a solder joint 120 with a reference ratio that is previously set (step S142).

When the ratio of the average height $H_{JOINT}$ of the solder joint 120 is lower than the reference ratio, the control section determines that the solder joint 120 is defective (step S151). On the contrary, when the ratio of the average height $H_{JOINT}$ of the solder joint 120 is equal to or higher than the reference ratio, the control section determines that the solder joint 120 is defective (step S152).

According to the method of inspecting a solder joint of the present invention, which is described above, it is determined whether the solder joint is defective by comparing the height of the solder joint in the estimated solder joint region with a reference height of a solder joint, which is previously set.

Therefore, it is not affected by image noises induced by the interference of environmental light and the interference of adjacent elements, so that exact inspection is possible to improve reliability of inspection.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method of inspecting a solder joint through which a lead of a semiconductor device is mounted on a printed circuit board, the lead extending from a body of the semiconductor device to over a pad of the printed circuit board in a longitudinal direction of the lead, the method comprising:
    setting an estimated solder joint region at an outside of an end of the lead of the semiconductor device, wherein the estimated solder joint region is set within a thickness region of the end of the lead in a cad data, and the end of the lead corresponds to an end of the longitudinal direction;
    capturing an image of the estimated solder joint region;
    calculating a height of the solder joint in the estimated solder joint region by using the captured image of the estimated solder joint region; and
    determining whether the solder joint is defective by comparing the height of the solder joint in the estimated solder joint region with a reference height of a solder joint, which is previously set.

2. The method of claim 1, wherein determining whether the solder joint is defective comprises:
    calculating a ratio of the height of the solder joint in the estimated solder joint region to the reference height of a solder joint, which is previously set; and
    determining whether the ratio of the solder joint is equal to or higher than a previously set ratio.

3. The method of claim 1, wherein the height of the solder joint in the estimated solder joint region is an average height of the solder joint in the estimated solder joint region.

4. The method of claim 1, wherein the reference height of the solder joint is a height of the estimated solder joint region.

5. The method of claim 2, wherein the height of the solder joint in the estimated solder joint region is an average height of the solder joint in the estimated solder joint region.

6. The method of claim 2, wherein the reference height of the solder joint is a height of the estimated solder joint region.

* * * * *